(12) United States Patent
Diez

(10) Patent No.: US 8,521,252 B2
(45) Date of Patent: Aug. 27, 2013

(54) METHOD FOR DISPLAYING A HOLLOW SPACE IN AN OBJECT UNDER INVESTIGATION

(75) Inventor: Michael Diez, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 1062 days.

(21) Appl. No.: 11/649,691

(22) Filed: Jan. 4, 2007

(65) Prior Publication Data

US 2007/0197897 A1   Aug. 23, 2007

(30) Foreign Application Priority Data

Jan. 13, 2006   (DE) .................. 10 2006 001 884

(51) Int. Cl.
*A61B 5/05* (2006.01)

(52) U.S. Cl.
USPC .......................................... 600/407; 600/424

(58) Field of Classification Search
USPC .................................. 600/407, 424
See application file for complete search history.

(56) References Cited

U.S. PATENT DOCUMENTS

| | | | |
|---|---|---|---|
| 5,720,291 A * | 2/1998 | Schwartz ..................... 600/456 |
| 6,211,798 B1 * | 4/2001 | Albrecht et al. .............. 340/990 |
| 6,254,588 B1 * | 7/2001 | Jones et al. ................... 604/525 |
| 6,317,621 B1 | 11/2001 | Graumann et al. |
| 6,700,773 B1 * | 3/2004 | Adriaansen et al. ..... 361/679.08 |
| 7,167,180 B1 * | 1/2007 | Shibolet ........................ 345/474 |
| 2004/0006268 A1 * | 1/2004 | Gilboa et al. ................. 600/424 |
| 2007/0016012 A1 * | 1/2007 | Hartlep et al. ................ 600/424 |

FOREIGN PATENT DOCUMENTS

| DE | 199 19 907 A1 | 11/2000 |
| DE | 10 2005 012 698 A1 | 8/2006 |

* cited by examiner

*Primary Examiner* — Tse Chen
*Assistant Examiner* — Vani Gupta

(57) ABSTRACT

The invention relates to a method for displaying a hollow space in an object under investigation, wherein the hollow space has an access point and a target point for a surgical instrument which can be introduced at least partially into the hollow space, and wherein a three dimensional image data set of a section of the hollow space having the access point and/or the target point is determined and spatially displayed. By highlighting the access point and/or the target point in the spatial display of the hollow space section it is possible to make a method available which provides the surgical staff with improved guidance in the object under investigation.

17 Claims, 1 Drawing Sheet

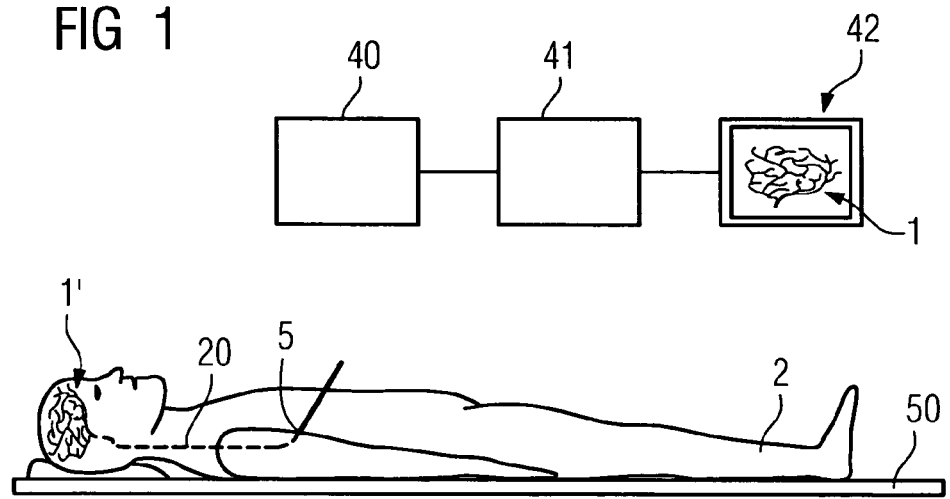

METHOD FOR DISPLAYING A HOLLOW SPACE IN AN OBJECT UNDER INVESTIGATION

CROSS REFERENCE TO RELATED APPLICATIONS

This application claims priority of German application No. 10 2006 001 884.2 filed Jan. 13, 2006, which is incorporated by reference herein in its entirety.

FIELD OF THE INVENTION

The invention relates to a hollow space wherein the hollow space has an access point and a target point for a surgical instrument which can be introduced at least partially into the hollow space, and wherein a three dimensional image data set of a section of the hollow space having the access point and/or the target point is determined and spatially displayed.

BACKGROUND OF THE INVENTION

Hollow spaces in an object under investigation, for example vascular pathologies, in particular intracranial vascular pathologies, are frequently dealt with by means of a catheter introduced into the femoral artery and fed via the blood vessels to the site of the lesion. As a rule the positioning and/or location of the catheter is performed using continuously pulsed X-ray transillumination to capture two dimensional projection data sets, together with the application of contrast medium. In so doing it often proves difficult for the neuroradiologist to reconcile the captured two dimensional projection data sets with the complex, three dimensional shape of the actual vascular tree.

Three dimensional images of a hollow space or hollow organ can nowadays be generated by various imaging modalities, such as magnetic resonance, computed tomography and 3D C-arm methods. Angiographic procedures are a suitable way of displaying blood vessels. In the case of 3D angiography, performed for example by means of a C-arm, a spatial display of the vascular tree is reconstructed and visualized from a plurality of preoperative or intraoperative two dimensional X-ray projection images captured from different angles. The recording techniques mentioned above provide the neuroradiologist with a spatial display of the hollow space system, for instance an intracranial vascular tree.

The gastrointestinal tract, trachea system, lymphatic system, bladder, ureter, blood vessel system etc. can be thought of as further examples of hollow spaces in the bodies of humans and animals that also include a hollow organ. There may also be other types of objects of investigation containing a hollow space or system of hollow spaces. The example of the surgical instrument designed as a catheter also needs to be taken into account.

Patent application DE 199 19 907 A1 discloses a method and a device for catheter navigation in three dimensional vascular tree recording, wherein the catheter position is determined by means of a miniaturized position detection system built into its tip and displayed in the 3-D view of the vascular tree recorded preoperatively and reconstructed in a navigation computer. The disadvantage of this method is that it does not provide the medical staff with a rapid means of guidance within the vascular tree recording.

SUMMARY OF THE INVENTION

The object of the invention is to provide a method of the type described in the introduction, providing the medical staff with improved guidance in the object being examined.

This object is achieved by an inventive method of the type described in the introduction, in that the access point and/or the target point is highlighted in the spatial display of the hollow space section. Highlighting of the access point and/or target point in the spatial display of the hollow space section is carried out as a rule by the medical staff. Not only the target point to be reached by the surgical instrument but also in appropriate cases the access point are highlighted in the spatial display. Highlighting the access point and target point proves to be advantageous when the medical staff need to be sure of their direction in a hollow space taking the form of a blood vessel system with a high degree of branching—such as a coronary or intracranial vascular tree. Highlighting makes the course of the blood vessel from the access point to the target point easier to recognize among a high number of branches and further blood vessels. For this it is not necessarily obligatory for a surgical instrument to be introduced into the hollow space section. However the method can be used during a surgical operation and for planning an operation.

The highlighting of an appropriate point is carried out for example on an input/output unit using for instance a mouse-controlled cursor on a monitor display surface where the spatial display of the hollow space section is visualized. The highlighted target and/or access points are then visualized in the spatial display, possibly by making them colored and flashing.

Advantageously the spatial display can be freely rotated on the monitor, a zoom function is provided, and intersecting planes through the spatially displayed hollow space section can be selected and viewed. This approach enables far simpler highlighting of the access point and/or target point, which is particularly advantageous in the case of intracranial vascular trees. Alternatively an automated method can be used to search for possible target points and highlight them as necessary in the display, including stenosis, aneurysms, etc.

In an advantageous embodiment of the invention, points of interest between the access and target points on the hollow space section are shown as highlighted reference points in the spatial display. These points can include narrowing of a blood vessel, bending of a blood vessel or the branching of blood vessels from the blood vessel connecting the access point and the target point. The highlighting of points of interest in the spatial display provides further reference points to assist in the guidance of surgical specialists, delivering valuable and easily recognizable information when an operation is being performed or planned.

In a further advantageous embodiment of the invention, a planned path for the surgical instrument from the access point to the target point in the hollow space section is highlighted in the spatial display. The planned path for the surgical instrument can be manually selected taking the existing situation into account, for example by the surgical specialists selecting a sufficient number of reference points for a special blood vessel connecting the access point and the target point.

Alternatively the blood vessel connecting the access point and the target point can be determined in spatial displays with the aid of structure detection software, and then be highlighted to particularly good advantage in the display, likewise with the aid of software.

The blood vessel to be highlighted can be determined according to defined criteria, such as the shortest path between the access point and the target point, or the path with the largest of the smallest blood vessel diameters, so as to enable a high degree of freedom of navigation, etc. For this purpose equidistant reference points on the blood vessel are established by software to determine the path, adjacent reference points being linked by a polygonal line. The distance between reference points needs to be chosen in such a way that within a tolerance range the polygonal line takes virtually the same course as the blood vessel needing to be highlighted.

Alternatively, highlighting can be applied manually by the user, by highlighting the blood vessel needing to be highlighted, for instance by means of a pointer on a touchscreen showing the spatial displays, and then displaying it complete with highlighting. Highlighting, in the sense of the improved visibility of an entire blood vessel or point, can be carried out using any means. For example the highlighting can be colored to make it stand out from the rest of the spatial display, or may flash periodically, or parts of the vascular tree may be hidden.

In a further advantageous embodiment of the invention the position and/or situation of at least one section of the introduced surgical instrument is determined and shown in the spatial display of the hollow space section. The method is used while a surgical operation is being performed. The blood vessel connecting the access and target points, or at least some section thereof, is highlighted in the display.

In addition, the position and/or situation of the introduced surgical instrument is determined during the surgical operation and shown in the spatial display. Advantageously the highlighted section in the spatial display of the hollow space section shows at least the introduced end of the surgical instrument. This makes it easier to recognize when the instrument is no longer being fed along the planned blood vessel—which as a rule is the highlighted one. This makes it easier to guide the instrument.

A deviation when guiding the surgical instrument during an operation can thus be more quickly and easily identified. The position and/or situation of the instrument can be shown by, for example, registration marks applied to the object under investigation, or by anatomically significant points.

In a preferred embodiment of the invention the hollow space section is displayed without the surroundings imposed by the object under investigation. For the purpose of the operation, potentially distracting anatomical background is removed from the spatial display of the hollow space section. This makes the display of the hollow space even clearer. For determining a vascular system or vascular tree displayed in this way, subtraction image methods can be used among other things to determine the spatial display of the hollow space section, or the magnetic resonance angiography method can also be used. By using a spatial display of a hollow space system showing only the hollow space system itself, the highlighting for the appropriate hollow space can be simplified, and if necessary the position and/or situation of the surgical instrument can be superimposed on the spatial display.

BRIEF DESCRIPTION OF THE DRAWINGS

Further advantages of the invention will emerge from an exemplary embodiment that is further explained with the aid of the accompanying drawings, in which FIG. 1 shows a device for determining a spatial display of a hollow space section FIG. 2 shows a spatial display of a hollow space section in the form of diagrams.

DETAILED DESCRIPTION OF THE INVENTION

FIG. 1 shows a device for determining the spatial display 1 of a hollow space in the form of a hollow organ 1' in a human body 2. In the exemplary embodiment, the hollow organ 1' of which a spatial display is to be determined takes the form of an intracranial vascular tree 1'. Data concerning the body 2 is captured by means of a recording unit 40 in order to determine a spatial display 1 of the intracranial vascular tree 1'. For this purpose the human body 2 is arranged on a couch 50. The recording unit 40 can be produced in numerous forms, such as a magnetic resonance device or a tomography-enabled C-arm.

When the recording unit 40 has captured the data, said data is available either as a three dimensional image data set, as in magnetic resonance methods, or is converted by suitable methods, such as back projection in the case of projection data sets recorded with X-rays, into a three dimensional image data set. For this purpose the data is passed to a data processing unit 41 and processed. A spatial display 1 of the measured hollow space section 1' in the object under investigation 2 is determined from the captured data and then displayed on an input/output unit 42.

An intracranial catheter 20 is then introduced into the human body 2 in FIG. 1. The intracranial catheter 20 is introduced through an access point 5 in the human body 2. In FIG. 1 the intracranial catheter 20 is introduced into the brachial artery in the upper arm and from there into the intracranial vascular tree 1'.

FIG. 2 is explained below in conjunction with the device shown in FIG. 1, the reference numbers of device components referring to said FIG. 1. FIG. 2 shows the spatial display 1 of an intracranial vascular tree 1', determined by means of the device described in FIG. 1. The intracranial vascular tree 1' is composed of a plurality of blood vessels which supply blood to the brain of an object under investigation 2—in this case a human patient—and are shown in the spatial display 1 as blood vessels 3. In this particular case the intracranial vascular tree 1' has a blood vessel exhibiting pathological narrowing.

This pathological narrowing, known as a stenosis, is defined by the medical staff with the aid of the spatial display 1 of the intracranial vascular tree 1' or by automated means with subsequent checking by the medical staff as target point 4, and has to undergo surgical treatment performed by medical staff using an intracranial catheter 20.

As a rule, before the surgical operation on the patient 2 a spatial display 1 of the intracranial vascular tree 1' is determined by for example computed tomography angiography, magnetic resonance angiography or 3D C-arm angiography. The spatial display 1 can if necessary visualize the entire vascular tree 1' from the target point 4 to an access point 5 through which the surgical instrument 20 is introduced into the patient 2. In the case of intracranial operations a section of the brachial artery may be used as the access point 5. A section of the femoral artery is frequently used as the access point for heart operations.

If the entire vascular tree 1' from the access point 5 to the target point 4 is recorded, it is preferably done at a single examination so as to avoid assembling displays of vascular tree subsections taken at relatively widely separated times.

The access point end of the vascular tree section is not completely shown in FIG. 2 and merely refers to the remote access point 5 for the intracranial catheter 20 on the right upper arm of the human body 2. In the exemplary embodiment the target point 4 is selected on a touchscreen 42 by the surgical staff with the aid of the spatial display 1 of the vascular tree 1'.

Highlighting is applied by exerting pressure at the appropriate point on the touchscreen 42. For the purpose of selecting the target point 4 the spatial display 1 can be freely rotated, and there is a facility to zoom in on sections of the spatial display 1. If the target point 4 is determined by selecting an appropriate section of blood vessel—in this case the narrowing—said target point is clearly highlighted in color in the spatial display 1. Once the target point 4 is established it is passed to a data processing unit 41.

With regard to guiding the instrument 20 from an access point 5 to a target point 4, a path 6 is selected for the surgical instrument 20 provided a plurality of options exist. The path 6 is established as a rule by surgical staff, for instance by highlighting further reference points for the blood vessel 3 established as the path 6 in the spatial display. Alternatively said blood vessel can also be determined with the aid of software, calculating for instance the shortest connection between the access point 5 and the target point 4, or the connection with the largest of the smallest diameters so as to avoid damaging the blood vessel. Contrast methods can be used for detecting the blood vessel 3 to be highlighted, or other methods for detecting structures in images may be used.

Furthermore critical points in the spatial display 1 of the blood vessel 3 connecting the access point 5 and the target point 4 are highlighted and shown in the spatial display 1 as branch points. Not all branch points in the blood vessel 3 connecting the access point 5 and the target point 4 are highlighted, but rather only those where there could be a risk of confusion when threading the intracranial catheter 20. This is the case for the branch points or reference points 7 to 10 highlighted in FIG. 2.

In addition to the reference points 7 to 10, the entire course of the blood vessel 3 connecting the access point 5 and the target point 4 can be shown in the spatial display 1 with highlighting 30.

Advantageously the highlighting 30 is applied using a computer, a starting point for the highlighting 30 being established in the same way as the access point 5, reference points 7 or 8 or 9 or 10 and target point 4 are established, as a rule manually. In FIG. 2 the starting point for the highlighting 30 is identical to the access point 5. With the aid of the established target point 4 and the starting point—in this case the access point 5—as well as the highlighted reference points 7 to 10, the blood vessel 3 concerned can be determined in the spatial display 1 by means of the data processing unit 41 and can for example be highlighted in color on the input/output unit 42.

Alternatively the highlighting 30 for a length of the blood vessel 3 connecting the access point 5 and the target point 4 can be applied manually by the surgical staff on the touchscreen 42, though as a rule this requires more time. The highlighting 30 for the blood vessel 3 connecting the access point 5 and the target point 4 makes it possible to obtain a very clear overview of the spatial course taken by the path 6 for the surgical instrument 20, together with an overview of significant or critical points on the course of said blood vessel.

When the spatial display 1 showing the highlighted blood vessel is used during an operation, the guidance provided to the surgical staff in the object under investigation 2 can be further improved. For this purpose the intracranial catheter 20 is located by means of an image-based method, for example. The position and/or situation of the surgical instrument 20 or the spatial display determined for the surgical instrument is superimposed on the spatial display 1 of the intracranial vascular tree 1' with highlighted path 6. To ensure the correct location and position for the superimposed image, as a rule the various coordinate systems need to be mutually registered. This may be achieved by appropriate calibration procedures.

By using a common spatial display 1 for the vascular tree 1' with the highlighted path 6 and the instrument position and/or situation, it is easy to check whether the surgical instrument 20 may have strayed too far from the highlighted blood vessel 3 or the planned path 6 and been fed along the wrong branch. If necessary, deviation from the position and/or situation of the surgical instrument 20 can be checked by automated means. If the position of the instrument 20 deviates—preferably the position of the guided end of the catheter 20—from the highlighted path 6, this can be visually and acoustically signaled to the surgical staff. Such a comparison can be made for example with the aid of a control unit (not shown in FIG. 1) which could also be responsible for allocating the coordinate systems.

It is even more advantageous if the vascular tree 1', the highlighting for the spatial display 1 and the surgical instrument 20 that is guided during the operation are determined in common, since this enables a different point in time for the capture of the instrument 20 and the vascular tree 1' to be avoided. This could be carried out by means of magnetic resonance angiography in conjunction with an electromagnetic location method.

By determining the coordinate systems consecutively, for example by suitably highlighting the patient 2, it is then possible to determine the spatial display 1 of the vascular tree 1', the highlighted blood vessel 3, and the position and/or situation of the intracranial catheter 20 in common. For this purpose it is necessary to transfer the target point 4 and possibly the access point 5 from preceding spatial displays 1 of the vascular tree 1' or vascular tree section to the next spatial display 1, so that the blood vessel 3 connecting the target point 4 and the access point 5 can be highlighted again by means of software.

By means of clearly visible highlighting 30 for the path 6 of the surgical instrument 20 and/or for the target point 4 and/or the access point 5, and further, reference points 7 to 10 in the spatial display 1 of the hollow space or hollow space system, the safety of the object under investigation 2 can be increased and the work of the surgical staff can be simplified.

The invention claimed is:

1. A method for displaying a vascular tree comprising blood vessels of a patient under a medical examination, the blood vessels forming a plurality of branching paths having an access point for inserting a surgical instrument connected to a target point to be reached by the surgical instrument traversing the vascular tree via threading the surgical instrument along a planned path through selected ones of the plurality of branching paths of the blood vessels of the vascular tree, comprising:

capturing image data about the vascular tree including the access point and the target point with a recording unit and determining with a data processing unit a three dimensional image data set of a section of the vascular tree containing the access point and the target point;

spatially displaying the three dimensional image data set as an image of the section of the vascular tree on a display which is coupled to receive the data from the data processing unit, wherein a first highlighting is applied to the access point and the target point and wherein the section of the vascular tree is displayed without a surrounding imposed by the patient to show only the vascular tree and removing an anatomical background of the patient;

determining a planned path between the access point and the target point traversing the selected ones of the plurality of branching paths of the blood vessels of the vascular tree in accord with defined criteria or by receiving user input defining the planned path;

displaying the planned path between the access point and the target point traversing the blood vessels of vascular tree in the image of the section of the vascular tree with a second highlighting relative to other data of the data set;

defining a plurality of points of interest in the image of the section of the vascular tree, wherein the points of interest comprise one or more critical branch points along the planned path traversing the blood vessels of the vascular tree consisting of a narrowing, a bending, or a branching of the blood vessels of the vascular tree connecting the access point to the target point where a risk of confusion exists for traversing the blood vessels of the vascular tree along the planned path via threading the surgical instrument through the blood vessels, wherein a third highlighting is applied to the points of interest in the image to assist in keeping the surgical instrument along the planned path in the blood vessels;

superimposing on the image of the vascular tree an indication of a position of the surgical instrument as it traverses the blood vessels of the vascular tree to the target point;

wherein the first, second, and third highlighting in the image of the section of the vascular tree is accomplished before the surgical instrument reaches the target point to provide a clear view of the planned path and an overview of critical points to assist in guidance of the surgical instrument as it traverses the blood vessels of the vascular tree to the target point; and signaling deviation of the surgical instrument from the planned path when the surgical instrument strays from the planned path into a wrong branch.

2. The method as claimed in claim 1, wherein an entire course connecting the access point and the target point is determined in the three dimensional image data set of the section of the vascular tree and highlighted in the display of the section of the vascular tree.

3. The method as claimed in claim 1, wherein the planned path is determined by establishing equidistant reference points connecting the access point with the target point and linking the equidistant reference points by a polygonal line.

4. The method as claimed in claim 1, wherein the planned path is input by a user of the surgical instrument via an input device comprising a touchscreen device or a graphical pointing device.

5. The method as claimed in claim 3, wherein the planned path is determined by a computer program.

6. The method as claimed in claim 1, wherein a position of a section of the surgical instrument is determined by means of an image-based method and is registered on the image using calibration procedures.

7. The method as claimed in claim 1, wherein the section of the vascular tree is displayed without a surrounding imposed by the patient using image subtraction methods.

8. The method as claimed in claim 1, wherein the highlighting is applied by a computer program.

9. The method as claimed in claim 1, wherein the highlighting is applied based on manual input received from a user of the surgical instrument.

10. The method as claimed in claim 1, wherein the highlighting appears as a color or a flash on the image.

11. The method as claimed in claim 1, wherein the vascular tree is a vascular tree of the patient.

12. A medical instrument for displaying a vascular tree of a patient under a medical investigation, the vascular tree comprising blood vessels forming a plurality of branching paths having an access point for inserting a surgical instrument connected to a target point to be reached by the surgical instrument traversing the vascular tree via threading the surgical instrument through selected ones of the plurality of branching paths of the blood vessels of the vascular tree, comprising:

a data processing unit that receives an image data set of a section of the vascular tree having the access point and the target point from a medical recording unit and transforms the image data set to a three dimensional data set of the section of the vascular tree; and a display unit coupled to receive the data from the data processing unit that displays the three dimensional data set as an image of the section of the vascular tree;

wherein the data processing unit is adapted to:
(a) display the section of the vascular tree without a surrounding imposed by the patient to show only the vascular tree and removing an anatomical background of the patient;
(b) output to the display unit a first highlighting for the access point and the target point;
(c) determine a planned path along the vascular tree between the access point and the target point for traversing the selected ones of the plurality of branching paths of the blood vessels of the vascular tree in accord with defined criteria or by receiving user input defining the planned path, and output to the display unit a second highlighting for the planned path;
(d) define a plurality of points of interest in the image of the section of the vascular tree, wherein the points of interest comprise one or more critical branch points along the planned path traversing the blood vessels of the vascular tree consisting of a narrowing, a bending, or a branching of the vascular tree connecting the access point to the target point where a risk of confusion exists for traversing the blood vessels of the vascular tree along the planned path via threading the surgical instrument therethrough, and output to the display unit a third highlighting for the points of interest in the image to assist in keeping the surgical instrument along the planned path in the blood vessels;
(e) receive an indication of a position of the surgical instrument as it traverses the blood vessels of the vascular tree to the target point and superimpose on the image of the vascular tree the position of the surgical instrument; and
(f) signal deviation of the surgical instrument from the planned path when the surgical instrument strays from the planned path into a wrong branch;

wherein the first, second, and third highlighting in the image of the section of the vascular tree is accomplished before the surgical instrument reaches the target point to provide a clear view of the planned path traversing the blood vessels of the vascular tree and an overview of critical points to assist in guidance of the surgical instrument as it traverses the blood vessels of the vascular tree to the target point.

13. The medical instrument as claimed in claim 12, wherein the planned path for the surgical instrument from the access point to the target point in the section of the vascular tree is highlighted in the display based on user input of the planned path.

14. The medical instrument as claimed in claim 12, wherein the position of the surgical instrument is determined by means of an image-based method and is registered on the image using calibration procedures.

15. The medical instrument as claimed in claim 12, further comprising a control unit that compares the position of the surgical instrument with the planned path and outputs a signal when the surgical instrument deviates from the planned path.

16. The medical instrument as claimed in claim 12, further comprising the surgical instrument.

17. The medical instrument as claimed in claim 12, further comprising the medical image recording unit that records the image data set of the section of the vascular tree having the access point and the target point.

* * * * *